United States Patent [19]

Cueman et al.

[11] Patent Number: 5,175,498
[45] Date of Patent: Dec. 29, 1992

[54] METHOD AND APPARATUS FOR MAKING SPATIALLY CORRELATED EDDY CURRENT MEASUREMENTS

[75] Inventors: Michael K. Cueman, Niskayuna; Donna C. Hurley, Albany, both of N.Y.; Paul B. Tuck, Wilmington, N.C.

[73] Assignee: General Electric Company, Schenectady, N.Y.

[21] Appl. No.: 489,152

[22] Filed: Mar. 5, 1990

[51] Int. Cl.$^5$ .................... G01N 27/72; G01R 33/12
[52] U.S. Cl. .................................. 324/225; 324/238
[58] Field of Search ............... 324/225, 219, 220, 221, 324/226, 227, 237, 238, 240, 241, 242

[56] References Cited

U.S. PATENT DOCUMENTS

| | | | |
|---|---|---|---|
| 2,882,488 | 4/1959 | Price et al. | 324/225 |
| 3,328,681 | 6/1967 | Wood | 324/225 |
| 4,909,091 | 4/1990 | Ellmann et al. | 324/220 |

Primary Examiner—Walter E. Snow
Attorney, Agent, or Firm—James R. McDaniel; Paul R. Webb, II

[57] ABSTRACT

Apparatus for measuring flaws in an object, such as a tube, having both an erratic motion, e.g. a back and forth oscillation, and a net axial motion has an idler wheel engaging the tube, and a digital rotary shaft encoder attached to the wheel. A POP circuit is coupled to the encoder. A pair of coils disposed around the object make up the active elements in an eddy current bridge. An ADC is coupled to both the bridge and POP circuit and corrects the signal from the bridge for motion complications. A method for doing same comprises sensing only the net motion of the object, detecting flaws in the object, providing an erratic motion complicated flaw signal, and correcting the flaw signal for the erratic motion.

13 Claims, 2 Drawing Sheets

5,175,498

METHOD AND APPARATUS FOR MAKING SPATIALLY CORRELATED EDDY CURRENT MEASUREMENTS

BACKGROUND OF THE INVENTION

The present invention relates to eddy current measurements of an object during manufacturing, and more particularly, flaw detection and characterization of a nuclear fuel tube having an irregular axial motion.

Zircaloy tubing is produced by cyclic cold working impacts in pilger mils to reduce the tube diameter. Thereafter additional steps are performed, e.g., annealing to relieve stress, etching to obtain a smooth outer surface, straightening, and polishing to remove small surface flaws. Finally, an "offline", i.e., after the total production process at a location separate from the process machines, eddy current flaw detector is used to reject tubes having flaws produced by the diameter reducing step. Because of the time required by the intermediate process, the pilger mills may produce a large quantity of defective tube before the problem is detected by the "offline" inspection. This delay in obtaining feedback can result in lost productivity and costly scrap. The delayed "offline" inspection is customarily employed because it is technically simple to implement.

For example, consider the eddy current signal due to a point defect on e tube which passes through a differential eddy current sensor, i.e., a pair of coils disposed about the tube at different axial positions and connected in a bridge circuit such that the impedance difference between the two coils is sensed. As the tube advances, the defect first passes through one coil of the differential eddy current sensor and drives the sensor output signal positive. In an offline scanner that moves the tube at a steady velocity, the same flaw passes through the second coil of the differential sensor a precise time later and it drives the output signal negative. The net effect of the passage of the defect is the sensor output signal having a single cycle of an updown waveform with a temporal period that can be calculated from the tube velocity and coil separation. This signal has a strong center frequency which can be easily enhanced by frequency domain filtering of the output voltage. Moreover, since the scanner moves all the tubes at a uniform velocity, all small flaws will have approximately this period. This technique can be equally well applied to other eddy current coil configurations.

It will be appreciated that it is desirable to inspect the tubing for flaws right after the diameter reducing step ("online") both to save the expense of the later steps for the inspected tube if it is flawed and toe able to immediately taken action to reduce the number of flaws in later processed tubes. However, the finished tube emerges from the pilger mill in uneven amounts due to an irregular axial motion, sometimes actually moving backward for short distances. In addition, mechanical coupling to the mill makes the tube vibrate perpendicular to its long axis. Moreover, the tube rotates irregularly about its axis and may also be bowed so that it rotates about the axis of the eddy current coils. All of these irregular motions result in artifacts in conventionally acquired eddy current data.

Two of these potential error sources can be handled by conventional engineering. Careful fixturing can reduce the effect of vibrations to a manageable level, and can reduce the effect of bowed tubing. Other rotational motion has no effect on the eddy current signal, due to the cylindrical symmetry of both the tubing and the encircling eddy current coil. However, fixturing cannot control the irregular axial motion of the product, and online scanning remains difficult at best.

In particular, the flaw will first drive the signal positive as it encounters the first coil of the differential sensor. The time lapse before the occurrence of the negative-going signal as the flaw passes through the second coil is now indeterminate. In fact, retrograde motion could even cause a section of tubing with a flaw to pass through the first coil several times before the second half of the sensor is reached. Thus the eddy current output signal, which is sampled at even time intervals, will be complicated by a motion artifact that no amount of careful fixturing will remove. The collection of useful signals with eddy current sensors mounted directly on the production mills is precluded by the erratic motion of the tubes during the diameter reducing pilger cycle. The tube motion also lowers the signal-to-noise ratio of the output signal.

It is therefore an object of the present invention to provide apparatus and method for making accurate measurements with a high signal-to-noise ratio on an irregularly moving object and to reduce the cost and increase the quality of the object when being processed.

SUMMARY OF THE INVENTION

In brief, these and other objects are achieved by apparatus for measuring flaws in an object having both erratic and net motions comprising means for sensing only the net motion of the object; means for detecting flaws in the object and for providing an erratic motion complicated flaw signal; and means, coupled to said sensing and detecting means, for correcting said flaw signal for the erratic motion and for providing an output flaw signal without the effects of said erratic motion.

A method in accordance with the invention for measuring flaws in an object having both erratic and net motions comprises sensing only the net motion of the object; providing an erratic motion complicated flaw signal; and correcting the flaw signal for the erratic motion.

DETAILED DESCRIPTION

Figure 1:
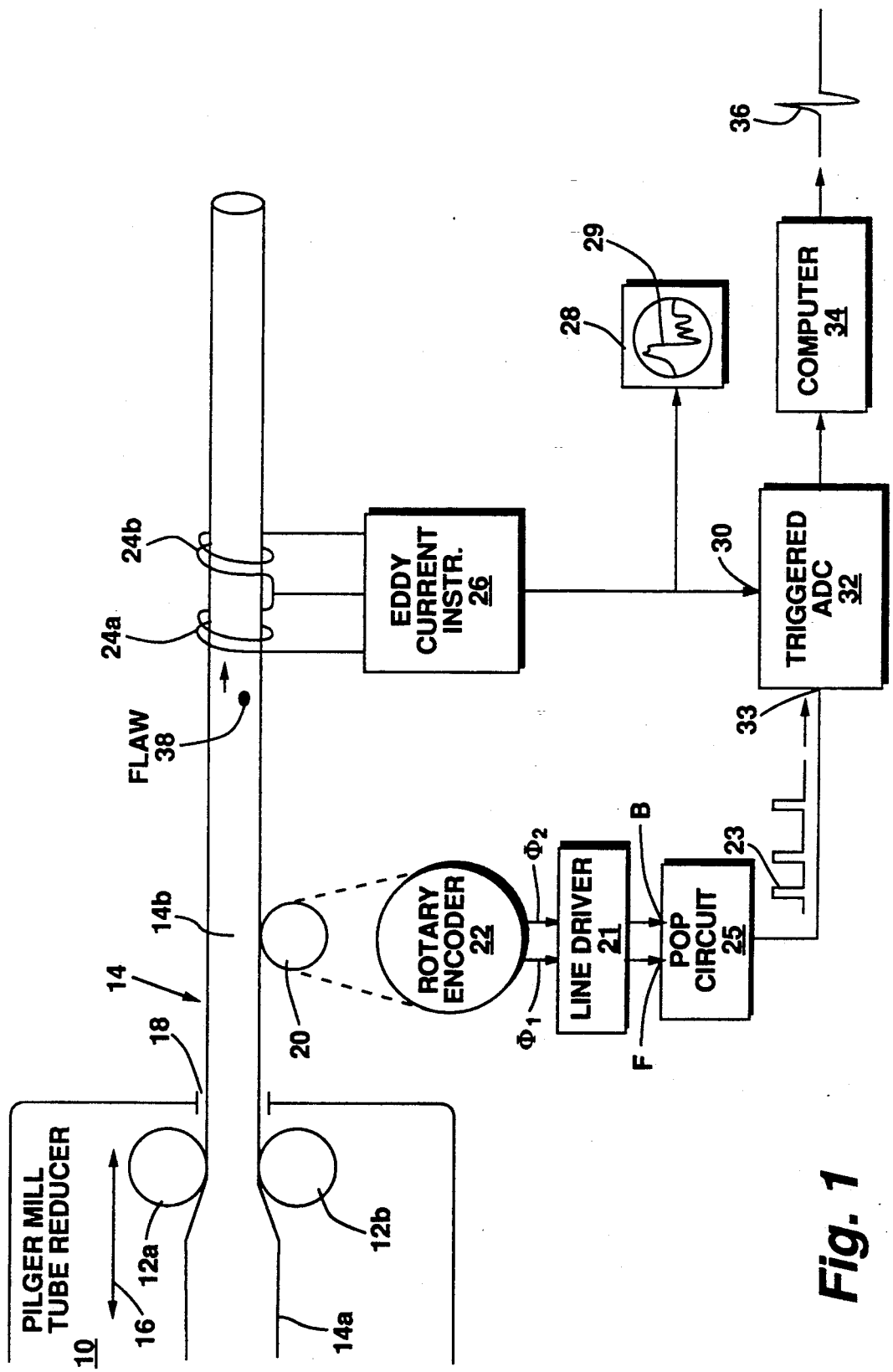
FIG. 1 is a block diagram of an embodiment of the invention.

In FIG. 1 a pilger mill tube reducer 10 comprises a pair of cold working driven rotating dies 12a and 12b. An object, such as a zircaloy nuclear fuel tube 14, has a large diameter section 14a, that passes between dies 12 and has its diameter reduced since dies 12 are spaced apart by less than the diameter of tube section 14a. During this diameter reducing step, irregular or erratic axial oscillatory motion of tube 14 occurs as indicated by arrow 16; however, there is a net axial movement to the right. Tube section 14b having a reduced diameter, emerges from an orifice 18 of mill 10.

A frictional idler wheel 20, e.g., made of rubber, frictional engages tube section 14b. A digital rotary shaft encoder 22, such as available from BEI Motion Systems, Goleta, Ga., is mechanically coupled to wheel 20 and provides output pulse trains I1 and I2 to a line driver 21, such as No. DM8830 also available from BEIK Motion Systems. In turn, line driver 21 provides output pulse trains F (tube 14 moving forward) and B (tube 14 moving backward) to pulse-on-position (POP) circuit 25. In turn, POP circuit 25 provides output pulses 23. Eddy current sensing coils 24a and 24b are disposed around tube section 14b proximate wheel 20 and are connected in a bridge circuit configuration. The bridge circuit is coupled to an eddy current bridge instrument 26 as is known in the art, e.g., model 25L made by the Nortec division of Stovely Instruments, Inc., Kennewick, Wash., and model MIZ-17 made by Zetec, Inc., Issaquah, Wash. Instrument 26 produces an eddy current output signal, which may be applied to a monitor display 28 and displayed as waveform 29 or to a strip chart recorder (not shown). The output signal from instrument 26 is also applied to an analog signal input 30 of a triggered analog-to-digital converter (ADC) 32. The pulses 23 are applied to a clock or trigger input 33 of ADC 32. The digital output signal from ADC 32 is applied to a computer 34, e.g., a microprocessor, that supplies a digital output signal, which is represented by waveform 36 in the drawing. If desired, computer 34 can be replaced with its hardwire digital or analog equivalent circuit.

In operation, encoder 22 provides two pulse train output signals, I1 and I2, phase shifted by 90 degrees relative to one another. The number of the pulses is directly related to the amount of rotation of the encoder 22 shaft and thus the rotation of the wheel 20. The direction of rotation, forward or backwards, determines which of the two pulse trains is phase shifted ahead of the other. The phase encoding technique is customary industrial encoder practice. Thus, a single phase of the pulse train from encoder 22 is not sufficient to distinguish between forward and backward motion. Therefore, the output pulse trains from encoder 22 are applied to line driver 21 to obtain the F and B pulse trains discussed above.

In order to trigger ADC 32 only in the case of the net forward motion and to accurately compensate for retrograde motion, both F and B output pulses must be monitored by pulse-on-position (POP) circuit 25. circuit 25 has been designed to use the dual pulse trains to derive a digital signal with pulses evenly spaced in relationship to only the net forward motion of the encoder shaft (and hence tube 14 to be inspected). The pulses 23 produced by the combination of encoder 22, line driver 21, and POP circuit 25 are used to trigger ADC 32. The resulting output signal from ADC 32 represents an evenly spaced record of the eddy current signal from tube 14, even though tube 14 may be moving erratically.

Figure 2:
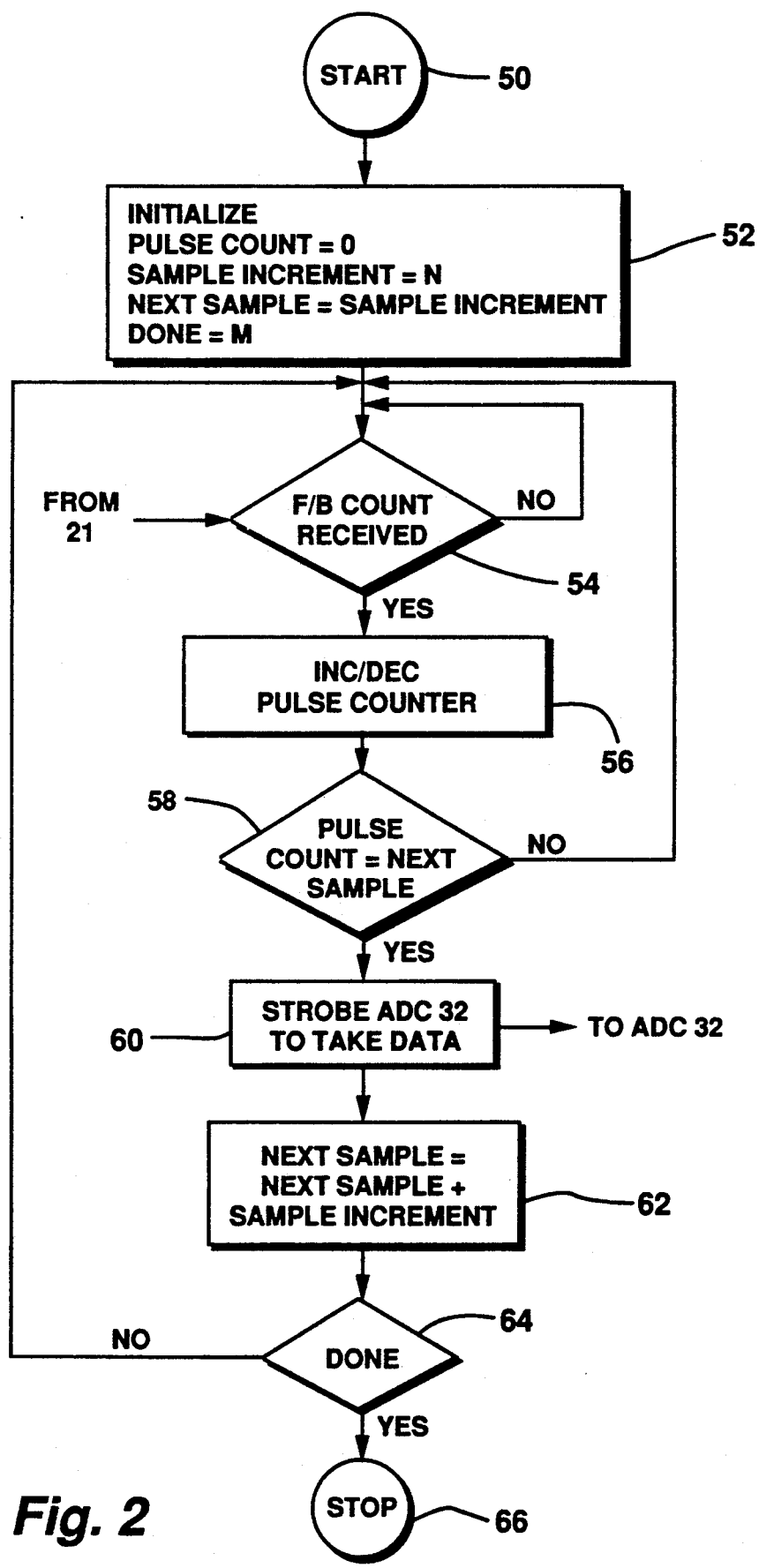
FIG. 2 is a flow chart of a POP circuit used in FIG. 1.

While POP circuit 25 can be implemented as hardwire digital logic, it can also be a microprocessor having a flow chart as shown in FIG. 2. The program starts at "start" circle 50. The initialization process box 52 shows the initialization steps. The "pulse count" is set to zero. A "sample increment" is set to N, e.g., 10, 20, 30, etc., pulses. The "next sample" (when the process starts) is set to "sample increment", which can be one, i.e., the first pulse, but can also be some number of other samples because e.g., tube 14 has an end cap which it is not desired to check for flaws. Then "done" is set to some number of samples M. Next, as indicated by decision block 54 a check is made to see if the F or B pulses are being received. If no, the program continues checking. If yes, a pulse counter is incremented if F pulses are received and decremented if B pulses are received, all as indicated by process box 56. Decision block 58 shows that if the pulse count in the counter is not equal to the "next sample" value the program loops back to block 54. If it is so equal, then process box 60 indicates that ADC 32 is triggered. Then process box 62 sets the value of "next sample" to the original value plus the "sample increment". Then as shown by decision box 64 a check is made to see if the process is "done", i.e., if the number of samples equals M. If not the program loops back to decision box 54. If yes, the program is stopped as indicated by circle 66.

It is understood that instead of using a fixed number of samples M to stop the program, a sensor (not shown) that detects the rear end of the tube 14 can be so used. Also, if the inspected object is a wire, the program might never stop as long as wire is being produced.

A flaw 38 as it passes under coil 24a will cause it to provide positive going signal, while coil 24b will provide a negative going signal when flaw 38 passes under it. Thus instrument 26 will provide an output signal, but one which is complicated by the erratic motion of tube 14 as shown by analog waveform 29. Waveform 29 may be viewed by an operator on display 28 to ensure that the diameter reduction step is operating as expected. More importantly, ADC 32 carries out its conversion operation only when triggered by pulses 23. Hence, the digital output signal from ADC 32 occurs at irregular intervals that correspond to the true net axial motion of tube 14. Thus, in this output signal from ADC 32, erratic motion artifacts are removed and signal-to-noise ratio is larger compared to waveform 29. This permits computer 34 to carry out standard digital processing, e.g. filtering using the fast Fourier transform, thresholding, etc., on output digital signal 36. The output signal from computer 34 can be coupled to an alarm (not shown).

It will therefore be appreciated that the present invention allows flaw detection of an erratically moving object, thereby saving the expense of later manufacturing steps on the flawed object. The invention also permits faster adjustments of mill 10 for higher quality (less flaws). In addition to tubes, the object can be other thin metal objects, e.g., tapes, wires, etc.

What is claimed is:

1. Apparatus for measuring flaws in an object having both erratic and net motions, said apparatus comprising:
   means for sensing only the net motion of the object;
   means for detecting flaws in the object and for providing an erratic motion complicated flaw signal; and
   means, coupled to said sensing and detecting means, for correcting said flaw signal for the erratic motion and for providing an output flaw signal without the effects of said erratic motion, wherein said correcting means is further comprised of a triggered analog-to-digital converter having a trigger responsive to said sensing means.

2. The apparatus of claim 1 wherein the object is tube.

3. The apparatus of claim 1 wherein said sensing means comprises an idler wheel adapted to frictionally engage the object, a rotary shaft encoder coupled to said wheel, a line driver coupled to said encoder, and a pulse-on-position circuit coupled to said line driver.

4. The apparatus of claim 1 wherein said detecting means comprises an eddy current bridge having a pair of coils adapted to be disposed proximate the object.

5. The apparatus of claim 4 wherein the object is a tube and said coils are disposed around the tube in axial spaced relationship.

6. The apparatus of claim 1 wherein said sensing means comprises an idler wheel adapted to engage the object, a digital rotary shaft encoder coupled to said wheel, a line driver coupled to said encoder, and a pulse-on-position circuit coupled to said line driver and to said converter; and said detecting comprises a bridge circuit coupled to said converter and having a pair of coils adapted to be disposed proximate the object.

7. Apparatus for measuring flaws in an object having both erratic and net axial motions, said apparatus comprising:
- an idler wheel adapted to frictionally engage the object;
- a rotary shaft encoder coupled to said wheel;
- a line driver coupled to said encoder;
- a pulse-on-position circuit coupled to said line driver;
- a bridge circuit having a pair of coils adapted to be disposed proximate the object; and
- a triggered analog-to-digital converter coupled to said pulse-on-position circuit and to said bridge.

8. The apparatus of claim 7 further comprising a display coupled to said bridge.

9. The apparatus of claim 7 further comprising a computer coupled to said converter.

10. A method for measuring flaws in an object having both erratic and net motions, said method comprising:
- sensing only the net motion of the object;
- providing an erratic motion complicated flaw signal; and
- correcting the flaw signal for the erratic motion, wherein said step of correcting is further comprised of the step of triggering an analog-to-digital conversion of said erratic motion complicated flaw signal responsive to said sensing of the net motion.

11. The method of claim 10 wherein said sensing step comprises rotating an idler wheel in accordance with the object motion, digitally encoding said rotation, and providing pulses representative only of the net motion of said object.

12. The method of claim 10 wherein said providing step comprises detecting eddy currents in the object.

13. The method of claim 10 wherein said sensing step comprises generating respective pulse trains indicating forward and backward motion of the object,
increasing a count if forward pulses are received and decreasing said count if backward pulses are received, and triggering said analog-to-digital converter when said count equals a selected value.

* * * * *